(12) United States Patent
Hirai

(10) Patent No.: US 7,332,306 B2
(45) Date of Patent: Feb. 19, 2008

(54) METHOD OF DETECTING PANCREATIC ISLET AMYLOID PROTEIN MUTANT GENE AND NUCLEIC ACID PROBE AND KIT THEREFOR

(75) Inventor: Mitsuharu Hirai, Kyoto (JP)

(73) Assignee: Arkray, Inc., Kyoto (JP)

( * ) Notice: Subject to any disclaimer, the term of this patent is extended or adjusted under 35 U.S.C. 154(b) by 0 days.

(21) Appl. No.: 10/553,614

(22) PCT Filed: Apr. 16, 2004

(86) PCT No.: PCT/JP2004/005509

§ 371 (c)(1),
(2), (4) Date: Oct. 18, 2005

(87) PCT Pub. No.: WO2004/092382

PCT Pub. Date: Oct. 28, 2004

(65) Prior Publication Data

US 2006/0275772 A1    Dec. 7, 2006

(30) Foreign Application Priority Data

Apr. 18, 2003  (JP) ............................. 2003-114380

(51) Int. Cl.
*C12P 19/34*  (2006.01)
*C07H 21/04*  (2006.01)

(52) U.S. Cl. .................................. 435/91.2; 536/24.31
(58) Field of Classification Search ..................... None
See application file for complete search history.

(56) References Cited

U.S. PATENT DOCUMENTS

2002/0106653 A1   8/2002   Kurane et al.

FOREIGN PATENT DOCUMENTS

| WO | WO 02/14555 | 2/2002 |
|---|---|---|
| WO | WO 02/072875 | 9/2002 |
| WO | WO 02/072875 A1 * | 9/2002 |
| WO | WO 03/100095 | 12/2003 |

OTHER PUBLICATIONS

Crockett et al., "Fluorescein-Labeled Oligonucleotides for Real-Time PCR: Using the Inherent Quenching of Deoxyguanosine Nucleotides," *Analytical Biochemistry*, 2001, vol. 290, pp. 89-97.*
Birch, et al. "The S20G Islet-Associated Polypeptide Gene Mutation in Familial NIDDM," *Diabetologia*, vol. 40, No. 9, p. 1113, Sep. 1997.
Howell, et al. "Dynamic Allele-Specific Hybridization: A New Method for Scoring Single Nucleotide Polymorphisms," *Nature Biotechnology*, Nature Publishing Group, New York, NY, vol. 17, No. 1, pp. 87-88, Jan. 1999.
Nazarenko, et al. "Effect of Primary and Secondary Structure of Oligodeoxyribonucleotides on the Fluorescent Properties of Conjugated Dyes," *Nucleic Acids Research*, Oxford University Press, Surrey, Great Britain, vol. 30, No. 9, pp. 2089-2195, May 2002.
Sakagashira, et al. "Missense Mutation of Amylin Gene (S20G) in Japanese NIDDM Patients," *Diabetes*, vol. 45, No. 9, pp. 1279-1281, Sep. 1996.
Torimura, et al. "Fluorescence-Quenching Phenomenon by Photoinduced Electron Transfer Between a Fluorescent Dye and a Nucleotide Base," *Analytical Sciences*, Japan Society for Analytical Chemistry, Tokyo, Japan, vol. 17, No. 1, pp. 155-160, Jan. 2001.
Loeffler, et al. "Rapid Detection of Point Mutations by Fluorescence Resonance Energy Transfer and Probe Melting Curves in *Candida* Species," *Clinical Chemistry*, vol. 46, No. 5, pp. 631-635, 2000.
Ma, et al. Enhanced in vitro Production of Amyloid-Like Fibrils from Mutant (S20G) Islet Amyloid Polypeptide,: *Amylolid*, vol. 8, pp. 242-249, 2001.

* cited by examiner

*Primary Examiner*—Kenneth R. Horlick
*Assistant Examiner*—Molly Baughman
(74) *Attorney, Agent, or Firm*—Knobbe, Martens, Olson & Bear, LLP

(57) ABSTRACT

A melting curve analysis is performed for a nucleic acid containing a mutation in a nucleotide sequence resulting in a mutation replacing serine at position 20 in an amino acid sequence of the pancreatic islet amyloid polypeptide with glycine (IAPP S20G), by using a nucleic acid probe of which end is labeled with a fluorescent dye, and in which fluorescence of the fluorescent dye decreases upon hybridization, wherein the nucleic acid probe has a nucleotide sequence complementary to a nucleotide sequence ending at the nucleotide number 247 in the nucleotide sequence of SEQ ID NO: 1 and having a length of 13 to 30 nucleotides, and the 5' end of the probe is labeled with the fluorescent dye, and measuring fluorescence of the fluorescent dye, and the mutation is detected on the basis of the result of the melting curve analysis.

9 Claims, 4 Drawing Sheets

Wild sequence    ggcaaatttttagttcattccGgcaacaactttggtgcattctctcat
Mutant sequence  ggcaaatttttagttcattccAgcaacaactttggtgcattctctcat

Fig. 1

Wild sequence    ggcaaattttttagttcattccAgcaacaactttggtgccattctctcat

Mutant sequence  ggcaaattttttagttcattccGgcaacaactttggtgccattctctcat caaagtttgttgcCggaatgaa caaagtttgttgcCggaat

SEQUENCE LISTING

<160> NUMBER OF SEQ ID NOS: 16

<210> SEQ ID NO 1
<211> LENGTH: 600
<212> TYPE: DNA
<213> ORGANISM: Homo sapiens
<220> FEATURE:
<221> NAME/KEY: allele
<222> LOCATION: 235

<400> SEQUENCE: 1

| | | | | | |
|---|---|---|---|---|---|
| aatctcagcc | atctaggtgt | ttgcaaacca | aaacactgag | ttacttatgt | gaaaattgtt | 60 |
| tctttggttt | tcatcaatac | aagatatttg | atgtcacatg | gctggatcca | gctaaaattc | 120 |
| taaggctcta | acttttcaca | tttgttccat | gttaccagtc | atcaggtgga | aaagcggaaa | 180 |
| tgcaacactg | ccacatgtgc | aacgcagcgc | ctggcaaatt | ttttagttca | ttccggcaac | 240 |
| aactttggtg | ccattctctc | atctaccaac | gtgggatcca | atacgtatgg | caagaggaat | 300 |

-continued

```
gcagtagagg ttttaaagag agagccactg aattacttgc ccctttagag gacaatgtaa      360
ctctatagtt attgttttat gttctagtga tttcctgtat aatttaacag tgcccttttc      420
atctccagtg tgaatatatg gtctgtgtgt ctgatgtttg ttgctaggac atataccttc      480
tcaaaagatt gttttatatg tagtactaac taaggtccca taataaaaag atagtatctt      540
ttaaaatgaa atgttttgc tatagatttg tattttaaaa cataagaacg tcattttggg       600

<210> SEQ ID NO 2
<211> LENGTH: 18
<212> TYPE: DNA
<213> ORGANISM: Artificial Sequence
<220> FEATURE:
<223> OTHER INFORMATION: primer

<400> SEQUENCE: 2
cacatgtgca acgcagcg                                                     18

<210> SEQ ID NO 3
<211> LENGTH: 24
<212> TYPE: DNA
<213> ORGANISM: Artificial Sequence
<220> FEATURE:
<223> OTHER INFORMATION: primer

<400> SEQUENCE: 3
ctcttgccat atgtattgga tccc                                              24

<210> SEQ ID NO 4
<211> LENGTH: 14
<212> TYPE: DNA
<213> ORGANISM: Artificial Sequence
<220> FEATURE:
<223> OTHER INFORMATION: probe

<400> SEQUENCE: 4
cattccggca acaa                                                         14

<210> SEQ ID NO 5
<211> LENGTH: 15
<212> TYPE: DNA
<213> ORGANISM: Artificial Sequence
<220> FEATURE:
<223> OTHER INFORMATION: probe

<400> SEQUENCE: 5
cattccggca acaac                                                        15

<210> SEQ ID NO 6
<211> LENGTH: 22
<212> TYPE: DNA
<213> ORGANISM: Artificial Sequence
<220> FEATURE:
<223> OTHER INFORMATION: probe

<400> SEQUENCE: 6
cattccagca acaactttgg tg                                                22

<210> SEQ ID NO 7
<211> LENGTH: 22
<212> TYPE: DNA
<213> ORGANISM: Artificial Sequence
<220> FEATURE:
<223> OTHER INFORMATION: probe
```

```
<400> SEQUENCE: 7
cattccggca acaactttgg tg                                            22

<210> SEQ ID NO 8
<211> LENGTH: 25
<212> TYPE: DNA
<213> ORGANISM: Artificial Sequence
<220> FEATURE:
<223> OTHER INFORMATION: probe

<400> SEQUENCE: 8
caccaaagtt gttgctggaa tgaac                                         25

<210> SEQ ID NO 9
<211> LENGTH: 22
<212> TYPE: DNA
<213> ORGANISM: Artificial Sequence
<220> FEATURE:
<223> OTHER INFORMATION: probe

<400> SEQUENCE: 9
gaatggcacc aaagttgttg cc                                            22

<210> SEQ ID NO 10
<211> LENGTH: 24
<212> TYPE: DNA
<213> ORGANISM: Artificial Sequence
<220> FEATURE:
<223> OTHER INFORMATION: probe

<400> SEQUENCE: 10
ctggaatgaa ctaaaaaatt tgcc                                          24

<210> SEQ ID NO 11
<211> LENGTH: 24
<212> TYPE: DNA
<213> ORGANISM: Artificial Sequence
<220> FEATURE:
<223> OTHER INFORMATION: probe

<400> SEQUENCE: 11
ccggaatgaa ctaaaaaatt tgcc                                          24

<210> SEQ ID NO 12
<211> LENGTH: 18
<212> TYPE: DNA
<213> ORGANISM: Artificial Sequence
<220> FEATURE:
<223> OTHER INFORMATION: probe

<400> SEQUENCE: 12
caaagttgtt gccggaat                                                 18

<210> SEQ ID NO 13
<211> LENGTH: 21
<212> TYPE: DNA
<213> ORGANISM: Artificial Sequence
<220> FEATURE:
<223> OTHER INFORMATION: probe

<400> SEQUENCE: 13
caaagttgtt gccggaatga a                                             21

<210> SEQ ID NO 14
<211> LENGTH: 18
```

```
<212> TYPE: DNA
<213> ORGANISM: Artificial Sequence
<220> FEATURE:
<223> OTHER INFORMATION: probe

<400> SEQUENCE: 14
caaagttgtt gctggaat                                                    18

<210> SEQ ID NO 15
<211> LENGTH: 50
<212> TYPE: DNA
<213> ORGANISM: Homo sapiens

<400> SEQUENCE: 15
ggcaaatttt ttagttcatt ccagcaacaa ctttggtgcc attctctcat                 50

<210> SEQ ID NO 16
<211> LENGTH: 50
<212> TYPE: DNA
<213> ORGANISM: Homo sapiens

<400> SEQUENCE: 16
ggcaaatttt ttagttcatt ccggcaacaa ctttggtgcc attctctcat                 50
```

US 7,332,306 B2

METHOD OF DETECTING PANCREATIC ISLET AMYLOID PROTEIN MUTANT GENE AND NUCLEIC ACID PROBE AND KIT THEREFOR

RELATED APPLICATIONS

This is the U.S. National Phase under 35 U.S.C. § 371 of International Application PCT/JP2004/005509, filed Apr. 16, 2004, which was published in a language other than English, which claims priority of JP 2003-114380, filed Apr. 18, 2003.

TECHNICAL FIELD

The present invention relates to method for detecting pancreatic islet amyloid polypeptide mutant gene, and a nucleic acid probe and a kit therefor.

BACKGROUND ART

The islet amyloid polypeptide (IAPP) is the major component of amyloid deposited in pancreatic islets of Type 2 diabetes patients with a high frequency, and is secreted by pancreatic islet β cells into blood together with insulin. The missense mutation replacing serine at position 20 in the amino acid sequence of IAPP with glycine is found in about 2.6% of Japanese Type 2 diabetes patients, in particular, in about 10% of young patients. The existence of the mutation is said to raise the risk of the diabetes onset.

If the mutation resulting in the S20G mutation in IAPP (also referred to as "IAPP S20G mutation") exists, a recognition site of a restriction enzyme emerges at the position of the mutation. Therefore, the mutation can be detected by a method of amplifying DNA by PCR so that a portion including the mutation position should be amplified, digesting the amplification product with a restriction enzyme and determining whether the DNA has been digested or not by electrophoresis (PCR-RFLP) (for example, refer to The Japanese Journal of Clinical Pathology, vol. 44, 8, pp. 778-782, 1996).

Because PCR amplifies templates of several molecules several billion times, even a trace amount of contaminant may cause a false positive or false negative result. In PCR-RFLP, the amplification product needs to be collected and subjected to a treatment with a restriction enzyme after PCR, and therefore the amplification product may contaminate the subsequent reaction system. Accordingly, a false positive or false negative result may be obtained.

Further, DNA is treated with a restriction enzyme and then subjected to electrophoresis after completion of PCR. Therefore, time required for the detection becomes extremely long. In addition, because the procedure is complicated, automatization is difficult.

Furthermore, a method is generally known in which a region containing a mutation is amplified by PCR, then a melting curve analysis is performed by using a nucleic acid probe labeled with a fluorescent dye, and the mutation is analyzed on the basis of the result of the melting curve analysis (Clinical Chemistry, vol. 46, 5, pp. 631-635, 2000; Japanese Patent Application Laid-open (Kokai) No. 2002-119291).

DISCLOSURE OF THE INVENTION

An object of the present invention is to identify a quenching probe effective for the detection of the IAPP S20G mutation and thereby provide a method for detecting the IAPP S20G mutation and a kit therefor.

The literature concerning the aforementioned method of using a probe only teaches that, concerning the design of the probe, the probe should be designed so that, when a quenching probe having an end labeled with a fluorescent dye hybridizes with a target nucleic acid, two or more nucleotide pairs of the probe-nucleic acid hybrid should form at least one pair of G and C in the end portion. With regard to the IAPP S20G mutation, the inventors of the present invention designed a quenching probe satisfying the aforementioned condition and attempted the detection. However, no quenching probe that enabled detection was easily obtained.

The inventors of the present invention found that by designing a quenching probe based on a specific region containing the IAPP S20G mutation, the IAPP S20G mutation could be detected by a melting curve analysis using the quenching probe.

The present invention provides the followings.

(1) A nucleic acid probe of which end is labeled with a fluorescent dye, and in which fluorescence of the fluorescent dye decreases upon hybridization, wherein the nucleic acid probe has a nucleotide sequence complementary to a nucleotide sequence ending at the nucleotide number 247 in the nucleotide sequence of SEQ ID NO: 1 and having a length of 13 to 30 nucleotides, and the 5' end of the probe is labeled with the fluorescent dye.

(2) The nucleic acid probe according to (1), wherein the nucleic acid probe has the nucleotide sequence of SEQ ID NO: 12 or 13.

(3) A method for detecting a mutation comprising performing a melting curve analysis for a nucleic acid having a single nucleotide polymorphism site by using a nucleic acid probe labeled with a fluorescent dye and measuring fluorescence of the fluorescent dye, and detecting the mutation on the basis of the result of the melting curve analysis, wherein the single nucleotide polymorphism is a mutation in a nucleotide sequence in a nucleic acid encoding a pancreatic islet amyloid polypeptide, resulting in a mutation replacing serine at position 20 in an amino acid sequence of the pancreatic islet amyloid polypeptide with glycine, and the nucleic acid probe is the nucleic acid probe as defined in (1) or (2).

(4) The method according to (3), wherein a region containing a single nucleotide polymorphism site in a nucleic acid contained in a sample is amplified to obtain the nucleic acid showing the single nucleotide polymorphism.

(5) The method according to (4), wherein the amplification is performed by a method of using a DNA polymerase.

(6) The method according to (5), wherein the amplification is performed in the presence of a nucleic acid probe.

(7) A kit for the method as defined in (3), which comprises a nucleic acid probe of which end is labeled with a fluorescent dye, and in which fluorescence of the fluorescent dye decreases upon hybridization, wherein the nucleic acid probe has a nucleotide sequence complementary to a nucleotide sequence ending at the nucleotide number 247 in the nucleotide sequence of SEQ ID NO: 1 and having a length of 13 to 30 nucleotides, and the 5' end of the probe is labeled with the fluorescent dye.

(8) The kit according to (7), wherein the nucleic acid probe has the nucleotide sequence of SEQ ID NO: 12 or 13.

(9) The kit according to (7) or (8), which further comprises a primer for amplifying a region containing a mutation in a nucleotide sequence in a nucleic acid encoding a pancreatic islet amyloid polypeptide, resulting in a mutation replacing serine at position 20 in an amino acid sequence of the pancreatic islet amyloid polypeptide with glycine, by a method of using a DNA polymerase.

BRIEF DESCRIPTION OF THE DRAWINGS

FIG. 1 shows positions of quenching probes that cannot identify a mutation.

BEST MODE FOR CARRYING OUT THE INVENTION

Figure 2:
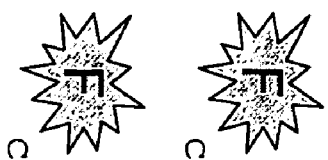
FIG. 2 shows positions of quenching probes that can identify a mutation.

<1> Probe of the Present Invention and Detection Method of the Present Invention The probe of the present invention is a nucleic acid probe of which end is labeled with a fluorescent dye, and in which fluorescence of the fluorescent dye decreases upon hybridization, wherein the probe has a nucleotide sequence complementary to a nucleotide sequence ending at the nucleotide number 247 in the nucleotide sequence of SEQ ID NO: 1 and having a length of 13 to 30 nucleotides, and the 5' end of the probe is labeled with the fluorescent dye.

In the present specification, a nucleotide sequence complementary to an objective nucleotide sequence means a nucleotide sequence complementary to the objective nucleotide sequence for the full length of the objective nucleotide sequence.

The probe of the present invention may be similar to the quenching probe described in Patent Document 1 except that it has a nucleotide sequence complementary to a nucleotide sequence ending at the nucleotide number 247 in the nucleotide sequence of SEQ ID NO: 1 (sequence having the mutant type nucleotide in the IAPP S20G mutation) and having a length of 13 to 30 nucleotides. Examples of the nucleotide sequence of the quenching probe used in the present invention include the nucleotide sequences of SEQ ID NOS: 12 and 13. As the fluorescent dye, those described in Patent Document 1 can be used, and specific examples thereof include FAM (trademark), TAMRA (trademark), BODIPY (trademark) FL and so forth. The fluorescent dye can be bound to an oligonucleotide in an ordinary manner, for example, by the method described in Patent Document 1.

The detection method of the present invention is a method for detecting a mutation by performing a melting curve analysis for a nucleic acid having a single nucleotide polymorphism site by using a nucleic acid probe labeled with a fluorescent dye and measuring fluorescence of the fluorescent dye, and detecting the mutation on the basis of the result of the melting curve analysis, and characterized in that the single nucleotide polymorphism is a mutation in a nucleotide sequence in a nucleic acid encoding a pancreatic islet amyloid polypeptide, resulting in a mutation replacing serine at position 20 in an amino acid sequence of the pancreatic islet amyloid polypeptide with glycine, and the nucleic acid probe is the probe of the present invention.

The detection method of the present invention can be performed according to usual methods for nucleic acid amplification and melting curve analysis (Tm analysis) except that a region containing the IAPP S20G mutation in a DNA encoding IAPP is amplified, and the probe of the present invention is used.

As the method for nucleic acid amplification, a method of using a polymerase is preferred, and examples thereof include PCR, ICAN, LAMP and so forth. When amplification is performed by a method using a polymerase, amplification is preferably performed in the presence of the probe of the present invention. The reaction conditions of the amplification and others can be easily adjusted depending on the used probe by those skilled in the art. In this method, only Tm of the probe is analyzed after amplification of a nucleic acid, and therefore it is not necessary to handle the amplification product after completion of the reaction. Thus, there is no risk of contamination with the amplification product. Further, because the detection is performed with the same equipment as required for the amplification, it is not even necessary to move a vessel. Therefore, automatization of the method is also easy.

The method will be further explained below by referring, as an example, to a case of using PCR. The primer pair used for PCR can be designed in the same manner as in a method for designing a primer pair in usual PCR except that it is designed so that a region to which the probe of the present invention is hybridizable should be amplified. The length and Tm of the primers are usually 10- to 40-mer and 40 to 70° C., preferably 15- to 25-mer and 55 to 60° C., respectively. Primers of the primer pair may not be equal in length. However, it is preferred that the Tm values of the primers are substantially equal (the difference is usually within 2° C.). The Tm values are values calculated by the nearest neighbor method. Examples of the primer pair include a primer pair comprising primers having the nucleotide sequences of SEQ ID NOS: 2 and 3.

PCR is preferably performed in the presence of the probe of the present invention. This enables the Tm analysis without performing any operation of handling the amplification product after completion of the amplification reaction. Tm values of primers and reaction conditions of PCR can be easily adjusted by those skilled in the art depending on the used probe.

A typical example of the composition of the reaction mixture for PCR is as follows.

TABLE 1

| | |
|---|---|
| DNA fragments | $10^1$ to $10^8$ molecules/reaction |
| Primers | 200 to 1000 nM |
| Probe | 100 to 1000 nM |
| Nucleotides | 20 to 200 μM each |
| DNA polymerase | 0.01 to 0.03 U/μl |
| Tris-HCl (pH 8.4 to 9.0) | 5 to 20 mM |
| MgCl$_2$ | 1.5 to 3 mM |
| KCl | 10 to 100 mM |
| Glycerol | 0 to 20% |

(Final fluid volume: 10 to 100 μl)

Further, a typical example of the temperature cycle is as follows, and this temperature cycle is usually repeated 25 to 40 times.

(1) Denaturation at 90 to 98° C. for 1 to 60 seconds
(2) Annealing at 60 to 70° C. for 10 to 60 seconds
(3) Extension at 60 to 75° C. for 10 to 180 seconds When annealing and extension are performed in one step, conditions of 60 to 70° C. for 10 to 180 seconds can be mentioned, for example.

The Tm analysis can be performed in a conventional manner except that fluorescence of the fluorescent dye binding to the probe of the present invention is measured. Fluorescence can be measured by using excitation light having a wavelength suitable for the fluorescent dye and measuring intensity of light of the emission wavelength. The temperature increasing rate in the Tm analysis is usually 0.1 to 1° C. per second. Composition of the reaction mixture for Tm analysis is not particularly limited so long as a probe and a nucleic acid having a sequence complementary to the nucleotide sequence of the prove can hybridize to each other. However, the monovalent cation concentration is usually 1.5 to 5 mM, and pH is usually 7 to 9. Because a reaction mixture for an amplification method using a DNA polymerase such as PCR usually satisfies these conditions, the reaction mixture after the amplification can be used as it is for the Tm analysis.

The IAPP S20G mutation can be detected on the basis of the results of the Tm analysis in an ordinary manner. The detection in the detection method of the present invention include not only detection of the presence or absence of a mutation, but also quantification of mutant type DNA and determination of the ratio of wild type DNA and mutant type DNA.

<2> Kit of the Present Invention

The kit of the present invention is a kit used for the second detection method of the present invention. This kit is characterized by including a nucleic acid probe of which end is labeled with a fluorescent dye and in which fluorescence of the fluorescent dye decreases upon hybridization (quenching probe), wherein the probe has a nucleotide sequence complementary to a nucleotide sequence ending at the nucleotide number 247 in the nucleotide sequence of SEQ ID NO: 1 and having a length of 13 to 30 nucleotides, and the 5' end of the probe is labeled with the fluorescent dye.

The quenching probe is as explained above with regard to the probe of the present invention.

The kit of the present invention may include reagents required for amplification of a nucleic acid in the detection method of the present invention, in particular, primers for amplification using a DNA polymerase, in addition to the quenching probe.

In the kit of the present invention, the quenching probe, primers and other reagents may be separately included, or a part thereof may be provided as a mixture.

EXAMPLES

The present invention will be explained more specifically with reference to the following examples.

Example 1

The primers shown in Table 2 were designed on the basis of the nucleotide sequence containing the S20G mutation of human IAPP gene (SEQ ID NO: 1) so that a region containing the S20G mutation could be amplified. In Table 2, the positions are indicated with the nucleotide numbers in the nucleotide sequence of SEQ ID NO: 1.

TABLE 2

| Primers Name | Sequence (5'→3') | mer | Position | SEQ ID NO: |
|---|---|---|---|---|
| F | Cacatgtgcaacgcagcg | 18 | 192-209 | 2 |
| R | Ctcttgccatatgtattggatccc | 24 | 296-273 | 3 |

Then, the probes having C at the ends shown in Table 3 were designed. In Table 3, the positions are indicated with the nucleotide numbers in the nucleotide sequence of SEQ ID NO: 1. Further, the capital letters in the nucleotide sequences represent sites of the IAPP S20G mutation, and (P) at the 3' ends means being phosphorylated. The probes were labeled with BODIPY (trademark) FL or TAMRA (trademark) in a conventional manner.

TABLE 3

| Probes Name | Sequence (5'→3') | Mer | Position | SEQ ID NO: |
|---|---|---|---|---|
| 5FL-mt-5-14 | (BODIPY FL)-cattccGgcaacaa-(P) | 14 | 229-242 | 4 |
| 5FL-mt-5-15 | (BODIPY FL)-cattccGgcaacaac-(P) | 15 | 229-243 | 5 |
| 5FL-wt-5-22 | (BODIPY FL)-cattccAgcaacaactttggtg-(P) | 22 | 229-250 | 6 |
| 5FL-mt-5-22 | (BODIPY FL)-cattccGgcaacaactttggtg-(P) | 22 | 229-250 | 7 |
| 3FL-wt-4-25 | caccaaagttgttgcTggaatgaac-(BODIPY FL) | 25 | 250-226 | 8 |
| 3FL-mt-3-22 | gaatggcaccaaagttgttgcC-(BODIPY FL) | 22 | 256-235 | 9 |
| 5FL-wt-2-24 | (BODIPY FL)-cTggaatgaactaaaaaatttgcc-(P) | 24 | 236-213 | 10 |
| 5FL-mt-2-24 | (BODIPY FL)-cCggaatgaactaaaaaatttgcc-(P) | 24 | 236-213 | 11 |
| 5FL-mt-1-21 | (BODIPY FL)-caaagttgttgcCggaatgaa-(P) | 21 | 247-227 | 12 |
| 5T-mt-1-21 | (6-TAMRA)-caaagttgttgcCggaatgaa-(P) | 21 | 247-227 | 12 |
| 5FL-mt-1-18 | (BODIPY FL)-caaagttgttgcCggaat-(P) | 18 | 247-230 | 13 |
| 5T-mt-1-18 | (6-TAMRA)-caaagttgttgcCggaat-(P) | 18 | 247-230 | 13 |
| 5FL-wt-1-18 | (BODIPY FL)-caaagttgttgcTggaat-(P) | 18 | 247-230 | 14 |

PCR and Tm analysis were performed by using a plasmid incorporated with a region of about 600 bp around the IAPP S20G mutation as a sample and Smart Cycler System (Cephied) under the conditions shown below. The excitation wavelength and the detection wavelength in the Tm analysis were 450 to 495 nm and 505 to 537 nm (BODIPY FL) and 527 to 555 nm and 565 to 605 nm (TAMRA), respectively.

TABLE 4

| Composition of reaction mixture | |
|---|---|
| $H_2O$ | 15.95 μL |
| 10 × Gene Taq buffer | 2.5 μL |
| 40% Glycerol | 3.125 μL |
| 10 mM each dATP, dUTP, dGTP, dCTP | 0.5 μL |
| 2 U/μL Uracil-N-glycosylase | 0.05 μL |
| 5 μM Probe | 1 μL |
| 100 mM $MgCl_2$ | 0.375 μL |
| 100 μM Primer F | 0.25 μL |
| 100 μM Primer R | 0.125 μL |

TABLE 4-continued

Composition of reaction mixture

| | |
|---|---|
| 5 U/μL Gene Taq FP | 0.125 μL |
| Sample (0 to 2000 copies) | 1 μL |
| Total | 25 μL |

TABLE 5

Reaction conditions

50° C., 2 min
↓
95° C., 2 min
↓
95° C., 1 sec
66° C., 18 sec (50 cycles)
↓
Tm analysis (1° C./sec)

PCR and Tm analysis were performed by using each probe. As a result, only when the probes 5FL-mt-1-18, 5T-mt-1-18, 5FL-mt-1-21 and 5T-mt-1-21 were used, changes in fluorescence intensity that could be analyzed in Tm analysis were observed. The positions of the probes relative to the nucleotide sequence containing the IAPP S20G mutation are shown in FIGS. 1 and 2. The wild type sequence (SEQ ID NO: 15) and mutant type sequence (SEQ ID NO: 16) shown in the drawings correspond to the nucleotide numbers 213 to 262 in the nucleotide sequence of SEQ ID NO: 1. Further, in the drawings, F denotes a fluorescent dye. On the basis of the positions shown in FIGS. 1 and 2, it is considered that whether the probe can be used for Tm analysis depends on the position of C bound with a fluorescent dye, and the length of the probe is not so important so long as the polymorphism site is included.

In the following, by using the probe 5FL-mt-1-21, sensitivity with respect to the absolute amount of genomic DNA, reproducibility and detection sensitivity with respect to ratio of the mutant type were examined.

Figure 3:
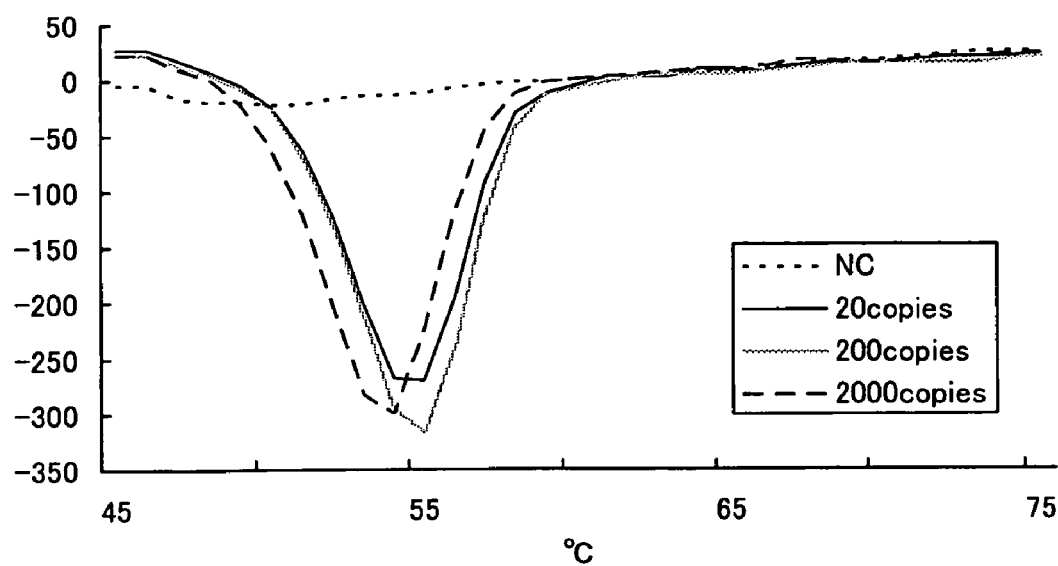
FIG. 3 shows sensitivity of the method of Example 1 with respect to the absolute amount of genomic DNA.

The above method was repeated by using samples containing 0, 20, 200 and 2000 copies of genomic DNA (wild type) instead of the plasmid. The results are shown in FIG. 3. As seen from FIG. 3, it is shown that the genomic DNA can be detected even if 20 copies.

Figure 4:
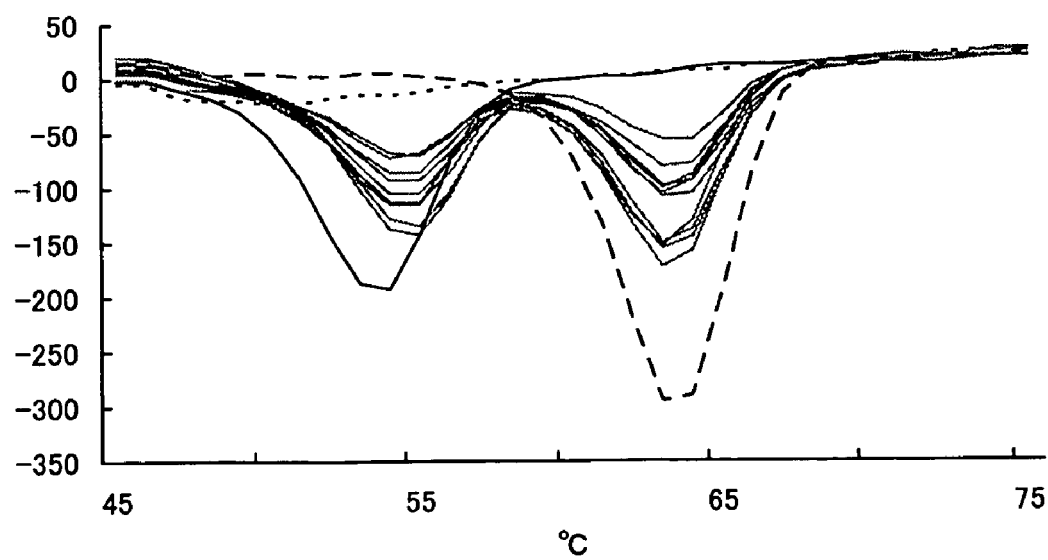
FIG. 4 shows reproducibility of the method of Example 1.

Then, plasmid having the wild type sequence (same as the above plasmid except that nucleotide number 285 is A in the nucleotide sequence of SEQ ID NO: 1) was prepared. Ten samples (wt/mt) were prepared by mixing the wild type plasmid and the mutant type plasmid. With respect to each of these samples as well as a sample (wt/wt) of only the wild type plasmid and a sample (mt/mt) of only the mutant type plasmid, the above method was repeated. The results are shown in FIG. 4. As seen from FIG. 4, it is shown that the method is excellent in the reproducibility.

Figure 5:
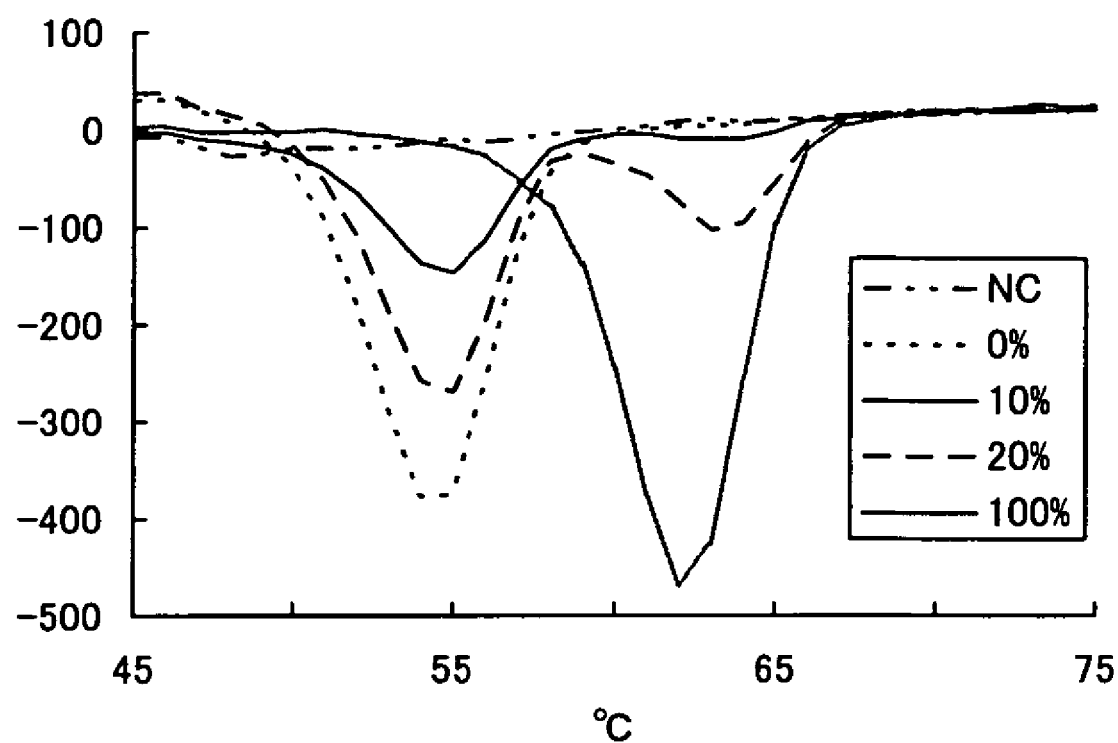
FIG. 5 shows detection sensitivity and quantitativeness of the method of Example 1 with respect to the ratio of the mutation type.

Furthermore, the method was repeated by changing the ratio of the wild type plasmid to the mutant type plasmid. The results are shown in FIG. 5. It is shown that the heights of both peaks change and the ratio can be determined based on the ratio of the heights of both peaks.

In FIGS. 3 to 5, the vertical axis represents a primary derivative value of fluorescence intensity with an inverted sign (−dF/dt), and the horizontal axis represents temperature (° C.).

INDUSTRIAL APPLICABILITY

According to the present invention, a quenching probe effective for detecting the IAPP S20G mutation is provided, and a method for detecting the IAPP S20G mutation by using it and a kit therefor are further provided. Because the Tm analysis is completed within several tens of seconds, time required for the detection can be markedly reduced. According to a preferred embodiment of the present invention, wherein amplification of nucleic acid in the presence of the probe and Tm analysis are combined, only the Tm of the probe is analyzed after the amplification of nucleic acid, and therefore it is not necessary to handle the amplification product after completion of the reaction. Accordingly, there is no risk of contamination with the amplification product. Further, because the detection can be performed with the same equipment as required for the amplification, it is even unnecessary to move a vessel. Therefore, automatization of the method is also easy.

What is claimed is:

1. A nucleic acid probe comprising a 5' end which is labeled with a fluorescent dye, and in which fluorescence of the fluorescent dye decreases upon hybridization, wherein the nucleic acid probe has a 5' end nucleotide complementary to nucleotide number 247 of SEQ ID NO:1 and has a nucleotide sequence complementary to 13 to 30 nucleotides 5' to nucleotide number 247 of SEQ ID NO:1, and wherein the 5' end of the probe is labeled with the fluorescent dye.

2. The nucleic acid probe according to claim 1, wherein the nucleic acid probe has the nucleotide sequence of SEQ ID NO: 12 or 13.

3. A method for detecting a mutation comprising performing a melting curve analysis for a nucleic acid having a single nucleotide polymorphism site by using a nucleic acid probe labeled with a fluorescent dye and measuring fluorescence of the fluorescent dye, and detecting the mutation on the basis of the result of the melting curve analysis, wherein the single nucleotide polymorphism is a mutation in a polynucleotide encoding a pancreatic islet amyloid polypeptide, resulting in a mutation replacing serine at position 20 in an amino acid sequence of the pancreatic islet amyloid polypeptide with glycine, and the nucleic acid probe is the nucleic acid probe as defined in claim 1.

4. The method according to claim 3, wherein a region containing the single nucleotide polymorphism site in a nucleic acid contained in a sample is amplified to obtain the nucleic acid showing the single nucleotide polymorphism.

5. The method according to claim 4, wherein the amplification is performed using a DNA polymerase.

6. The method according to claim 5, wherein the amplification is performed in the presence of a nucleic acid probe.

7. A kit for the method as defined in claim 3, comprising a nucleic acid comprising an end which is labeled with a fluorescent dye, and in which fluorescence of the fluorescent dye decreases upon hybridization, wherein the nucleic acid probe has a 5' end nucleotide complementary to nucleotide number 247 of SEQ ID NO:1 and has a nucleotide sequence complementary to 13 to 30 nucleotides 5' to nucleotide number 247 of SEQ ID NO:1, and wherein the 5' end of the probe is labeled with the fluorescent dye.

8. The kit according to claim 7, wherein the nucleic acid probe has the nucleotide sequence of SEQ ID NO: 12 or 13.

9. The kit according to claim 7, which further comprises a primer for amplifying a region containing a mutation in a polynucleotide encoding a pancreatic islet amyloid polypeptide, resulting in a mutation replacing seine at position 20 in an amino acid sequence of the pancreatic islet amyloid polypeptide with glycine, using a DNA polymerase.

* * * * *

UNITED STATES PATENT AND TRADEMARK OFFICE
CERTIFICATE OF CORRECTION

| | |
|---|---|
| PATENT NO. | : 7,332,306 B2 |
| APPLICATION NO. | : 10/553614 |
| DATED | : February 19, 2008 |
| INVENTOR(S) | : Mitsuharu Hirai |

Page 1 of 1

It is certified that error appears in the above-identified patent and that said Letters Patent is hereby corrected as shown below:

On the Title Page , Item (56) "Other Publications," Line 26, "*Amylolid*, vol. 8," should be changed to --*Amyloid*, vol. 8,--

Column 6, Line 52, "(Cephied) under the" should be changed to --(Cepheid) under the--

Column 14, Line 49, "replacing seine at" should be replaced with --replacing serine at--

Signed and Sealed this

Ninth Day of September, 2008

JON W. DUDAS
*Director of the United States Patent and Trademark Office*